United States Patent
Stoer et al.

(10) Patent No.: US 10,052,272 B2
(45) Date of Patent: Aug. 21, 2018

(54) COMPOSITION COMPRISING ISOSORBIDE MONOOLEATE

(71) Applicant: BASF SE, Ludwigshafen (DE)

(72) Inventors: Claudia Stoer, Solingen (DE); Claus Nieendick, Krefeld (DE); Markus Weissenegger, Duesseldorf (DE); Daniela Prinz, Dormagen (DE); Mirella Winzek, Titz (DE); Jennifer Schoss, Erkrath (DE); Markus Dierker, Duesseldorf (DE); Norbert Boyxen, Kempen (DE); Ute Griesbach, Düsseldorf (DE); Werner Seipel, Hilden (DE); Werner Mauer, Sendenhorst-Albersloh (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 15/323,750

(22) PCT Filed: Jul. 1, 2015

(86) PCT No.: PCT/EP2015/064944
§ 371 (c)(1),
(2) Date: Jan. 4, 2017

(87) PCT Pub. No.: WO2016/005239
PCT Pub. Date: Jan. 14, 2016

(65) Prior Publication Data
US 2017/0135931 A1    May 18, 2017

(30) Foreign Application Priority Data
Jul. 11, 2014    (EP) ..................... 14176684

(51) Int. Cl.
| | | |
|---|---|---|
| *A61K 8/368* | (2006.01) | |
| *A61K 8/44* | (2006.01) | |
| *A61K 8/49* | (2006.01) | |
| *A61K 8/60* | (2006.01) | |
| *A61Q 19/10* | (2006.01) | |
| *C11D 1/90* | (2006.01) | |
| *C11D 3/22* | (2006.01) | |
| *A61K 8/36* | (2006.01) | |
| *A61K 8/46* | (2006.01) | |
| *A61K 8/19* | (2006.01) | |

(52) U.S. Cl.
CPC .............. *A61K 8/4973* (2013.01); *A61K 8/19* (2013.01); *A61K 8/36* (2013.01); *A61K 8/368* (2013.01); *A61K 8/44* (2013.01); *A61K 8/463* (2013.01); *A61K 8/602* (2013.01); *A61Q 19/10* (2013.01); *A61K 2800/596* (2013.01)

(58) Field of Classification Search
CPC . A61K 8/368; A61K 8/44; A61K 8/49; A61K 8/4973; A61K 8/60; A61Q 19/10; C11D 1/662; C11D 1/90; C11D 3/2093; C11D 3/22
See application file for complete search history.

(56) References Cited

U.S. PATENT DOCUMENTS

2015/0030553 A1    1/2015  Pilz et al.

FOREIGN PATENT DOCUMENTS

| DE | 19 543 633 A1 | 5/1997 | |
|---|---|---|---|
| WO | WO-2010/115565 A1 | 10/2010 | |
| WO | WO-2013/017255 A1 | 2/2013 | |
| WO | WO-2013/017263 A1 | 2/2013 | |
| WO | WO 2013/041388 * | 3/2013 | ........... C07D 493/04 |
| WO | WO-2013/041388 A1 | 3/2013 | |

OTHER PUBLICATIONS

International Search Report for Patent Application No. PCT/EP2015/064944, dated Oct. 1, 2015.

* cited by examiner

*Primary Examiner* — Brian P Mruk
(74) *Attorney, Agent, or Firm* — Marshall, Gerstein & Borun LLP

(57) ABSTRACT

The present invention relates to a composition comprising isosorbide monooleate, a first surfactant selected from the group consisting of an alkyl glycoside having a weight average of the number of C-atoms in the alkyl chain of more than 11, cocoamidopropyl betaine and mixtures thereof, a second surfactant which is an alkyl glycoside having a weight average of the number of C-atoms in the alkyl chain of less than 11 and water. Furthermore it relates to a process for making this composition and to a cosmetic formulation, comprising this composition.

20 Claims, No Drawings

COMPOSITION COMPRISING ISOSORBIDE MONOOLEATE

CROSS-REFERENCE TO RELATED APPLICATIONS

This is the U.S. national phase of International Patent Application No. PCT/EP2015/064944, filed Jul. 1, 2015, which claims the benefit of European Patent Application No. 14176684.0, filed Jul. 11, 2014.

The present invention relates to a composition comprising isosorbide monooleate, a first surfactant selected from the group consisting of an alkyl glycoside having a weight average of the number of C-atoms in the alkyl chain of more than 11, cocoamidopropyl betaine and mixtures thereof, a second surfactant which is an alkyl glycoside having a weight average of the number of C-atoms in the alkyl chain of less than 11 and water. Furthermore it relates to a process for making this composition and to a cosmetic formulation, comprising this composition.

Cosmetic formulations, detergents and cleansers comprising isosorbide monooleate, i. e. the monoester of isosorbide and oleic acid, are known. Isosorbide monooleate has many advantageous properties which are the reason why isosorbide monooleate is used in cosmetic formulations, in detergents and in cleansers.

WO 2010/115565 (EP 2 239 315) discloses detergents and cleansers comprising isosorbide monoesters. In the example section a formulation comprising 1% by weight isosorbide monoester and 3% by weight coco glucoside is disclosed.

WO 2013/041388 discloses cosmetic formulation s comprising isosorbide monooleate, specifically disclosed is a formulation comprising 1% by weight isosorbide monooleate and 1.5% by weight coco glucoside (FIG. 4). This formulation has good foaming performance.

European patent application no. 14154978 filed on Feb. 13, 2014 (BASF internal file no. PF 75368) discloses a microemulsion comprising isosorbide monooleate and caprylyl/capryl glucoside and lauryl glucoside. It is disclosed that isosorbide monooleate which is used commercially is generally a mixture of monoester, diester, isosorbide and fatty acids, mainly oleic acid.

DE 1 9543 633 A1 discloses cosmetic formulations comprising partial esters of fatty acids and glycerol and alkly glycosides.

It is a disadvantage of isosorbide monooleate that it is a wax having a melting point of about 33° C. and that it is therefore difficult to incorporate isosorbide monooleate into formulations. At ambient temperature (20° C.) dissolving the solid isosorbide monooleate takes a long time. Alternatively formulations containing isosorbide monooleate can be produced at elevated temperature so that isosorbide monooleate can be added as a liquid.

The problem underlying the present invention therefore is to provide isosorbide monooleate in a form that allows its incorporation into formulations at a temperature of not more than 30° C., preferably at ambient temperature, in an easy way and to provide a process that allows easy production of cosmetic formulations comprising isosorbide monooleate at a temperature of not more than 30° C., preferably at ambient temperature.

This problem is solved by the composition according to the present invention. The composition according to the present invention is a first subject of the present invention.

The composition according to the present invention comprises 15-35% by weight, preferably 20-30% by weight, more preferably 23-28% by weight, isosorbide monooleate, 10-30% by weight, preferably 15-25% by weight, more preferably 17-22% by weight, of a first surfactant selected from the group consisting of an alkyl glycoside having a weight average of the number of C-atoms in the alkyl chain of more than 11, preferably more than 12, cocoamidopropyl betaine and mixtures thereof, 10-30% by weight, preferably 15-25% by weight, more preferably 17-22% by weight, of a second surfactant which is an alkyl glycoside having a weight average of the number of C-atoms in the alkyl chain of less than 11, preferably less than 10, optionally an acid in an amount so that the pH value of the composition is 3 to 7, wherein the acid preferably is an organic acid, more preferably an acid selected from the group consisting of citric acid, lactic acid and a mixture thereof, 0-5% by weight, preferably 0-2% by weight, more preferably 0-1% by weight, more preferably 0% by weight, further cosmetically acceptable ingredients, ad 100% by weight water.

A pH value of 3 to 7 is favourable because isosorbide monooleate is not hydrolyzed in relevant amounts under these conditions.

In one embodiment of the present invention the composition according to the present invention is not a microemulsion.

A microemulsion is a special type of emulsion which comprises at least one surfactant, at least one oil (i. e. a lipophilic liquid at 25° C. having a solubility in water of not more than 2% by weight at 20° C.), and water and which is thermodynamically stable (contrary to ordinary emulsions), and which is macroscopically homogeneous and optically transparent.

In one embodiment of the present invention the composition according to the present invention comprises less than 5% by weight, preferably less than 2% by weight, more preferably 0% by weight, of an oil, wherein an oil is a lipophilic substance which is liquid at 25° C. and which has a solubility in water of not more than 2% by weight at 20° C. Isosorbide dioleate is not to be considered as oil as defined in this paragraph, i. e. if, in the most preferred embodiment, the present invention comprises 0% by weight of an oil, it may still comprise isosorbide dioleate.

The composition according to the present invention has many advantages. It provides isosorbide monooleate in a form that allows its incorporation into formulations at a temperature of not more than 30° C. The other components of the composition according to the present invention are desired in many cosmetic formulations, detergents or cleansers. Therefore the presence of these other components is not a disadvantage.

The composition according to the present invention is a cold processable, easy to handle, pumpable blend.

The composition according to the present invention can be made by a process comprising mixing the isosorbide monooleate, the first surfactant, the second surfactant, optionally the acid, optionally the further cosmetically acceptable ingredients and water, preferably at a temperature of more than 20° C., more preferably at a temperature at which the isosorbide monooleate is liquid. This process for making the composition according to the present invention is another subject of the present invention.

Isosorbide monooleate can be made as disclosed in WO 2010/115565 or by other known esterification methods.

Isosorbide monooleate according to the present invention generally is a mixture comprising (pure) isosorbide monooleate as major component and additionally isosorbide dioleate, oleic acid and isosorbide. In this mixture the oleic acid, which is generally obtained from plants, also is a mixture comprising oleic acid as major component and other fatty acids in minor amounts. The term pure isosorbide monooleate means the monoester of isosorbide with a fatty acid mixture comprising oleic acid as major component. Here, major component means more than 65% by weight, preferably more than 70% by weight, more preferably more than 75% by weight, oleic acid. Therefore, in one embodiment of the present invention the isosorbide monooleate is a mixture comprising pure isosorbide monooleate in an amount of 65-95% by weight, preferably 65-85% by weight, more preferably 65-75% by weight. The amounts in % by weight can be determined by gas chromatography (GC) with appropriate calibration. In this pure isosorbide monooleate the fatty acid moieties comprise more than 65% by weight, preferably more than 70% by weight, more preferably more than 75% by weight, oleic acid moieties. The amounts in % by weight can be determined by gas chromatography (GC) with appropriate calibration.

It can be advantageous if the isosorbide monooleate is a mixture comprising pure isosorbide monooleate in an amount of 65-95% by weight, preferably 65-85% by weight, more preferably 65-75% by weight. It was observed in experiments that compositions according to the present invention comprising isosorbide monooleate that comprises pure isosorbide monooleate in an amount of 60% by weight resulted in phase separation over time, whereas a content of 77% by weight pure isosorbide monooleate resulted in stable compositions showing no phase separation, whereas a content of more than 95% by weight pure isosorbide monooleate resulted in compositions that were difficult to handle due to their gel-like behavior.

In one embodiment of the present invention the alkyl glycosides present in the composition are alkyl glucosides, wherein the degree of oligomerization (number average) of the glucose moiety preferably is between 1 and 2.

In one embodiment of the present invention the alkyl glycoside having a weight average of the number of C-atoms in the alkyl chain of more than 11 is coco glucoside, i. e. the fatty acid moieties are obtained from coconut oil, so that the lauryl moiety is the major component (i. e. at least 50% by weight, preferably at least 60% by weight, more preferably at least 70% by weight, of all fatty acid moieties are lauryl moieties), and the saccharide moiety is a glucose moiety.

In one embodiment of the present invention the composition according to the present invention has a viscosity of between 1000 and 10000 mPas, preferably between 1500 and 8000, more preferably between 2,000 and 6,000 mPas (determined with a Brookfield RVT viscometer, spindle 5, 20 rpm, at 20° C.).

Another subject of the present invention is a process for making a cosmetic formulation, e. g. a shampoo or a bodywash formulation, comprising contacting the composition according to the present invention with further cosmetically acceptable ingredients, preferably at a temperature of less than 30° C., so that the cosmetic formulation is obtained.

In one embodiment of the present invention the composition according to the present invention has a foam boosting effect in the cosmetic formulation in which the composition according to the present invention is incorporated. Accordingly, another subject of the present invention is the use of the composition according to the present invention as foam booster in cosmetic formulation.

The composition according to the present invention can also be used to make formulations that can be used as care additive in liquid fine fabric detergents, or for soil removal, or as pre-treatment formulation for stain removal on textiles, or for enhanced oil recovery, or as solubilizer for active ingredients in unpolar substances.

Another subject of the present invention is a cosmetic formulation, e. g. a shampoo or a bodywash formulation, comprising the composition according to the present invention, preferably in an amount of 0.5 to 10% by weight, more preferably 1 to 8% by weight, more preferably 1 to 6% by weight, and further cosmetically acceptable ingredients.

A cosmetically acceptable ingredient can be any cosmetically acceptable ingredient. It can be a cosmetically acceptable ingredient as disclosed in WO 2013/041388 or in European patent application no. 14154978.

According to the present invention the term alkyl glycoside means the reaction product of monosaccharides and fatty alcohols. A fatty alcohol is a linear, primary monoalkanol having 6 to 22 carbon atoms, optionally comprising up to 3 double bonds. A monosaccharide can be an aldose or a ketose, for example glucose, fructose, mannose, galactose, talose, gulose, allose, altrose, idose, arabinose, xylose, lyxose or ribose. The aldoses are preferably used by virtue of their better reactivity. Among the aldoses, glucose is particularly suitable because it is readily obtainable and available in industrial quantities. The alkyl glycosides produced with glucose are alkyl glucosides. Alkyl glycosides, depending on the specific process for making them, can comprise oligosaccharide moieties. Therefore, the terms alkyl oligoglycoside, alkyl polyglycoside, alkyl oligosaccharide and alkyl polysaccharide are used for alkyl glucosides in which an alkyl radical is attached to more than one glycose residue, i.e. to a poly- or oligosaccharide residue. These names are regarded as synonymous with one another. Accordingly, an alkyl monoglycoside comprises a monosaccharide moiety. Since mixtures are generally obtained in the acid-catalyzed reaction of sugars and fatty alcohols, the name alkyl glycoside is used in the following both for alkyl mono-glycosides and also for alkyl poly- or oligo-glycosides and, in particular, mixtures thereof. Alkyl glycosides have the formula $R^1—O—S_n$, wherein $R^1$ is an alkyl moiety derived from a fatty alcohol which is bound to the mono- or oligo-saccharide moiety. It is assumed that this bond is an acetal bond, it is also conceivable that it is a hemiacetal bond or an ether bond. The degree of oligomerization of the saccharide moiety is denoted by n. Values between 1 and 5 (on average) are common. The average is a number average.

Cocoamidopropyl betaine is an amphoteric surfactant obtainable by reacting fatty acids obtained from coconut oil with dimethylaminopropylamine and subsequently with chloroacetic acid. Lauramidopropyl betaine is the major component of cocoamidopropyl betaine and hast the following formula:

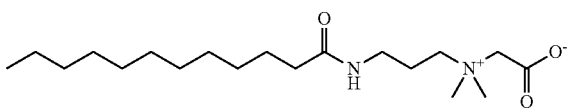 [SMILES: CCCCCCCCCCCC(=O)NCCC[N+](C)(C)CC(=O)[O-]]

According to the present invention cocoamidopropyl betaine is a mixture comprising at least 50% by weight, preferably at least 60% by weight, more preferably at least 70% by weight lauramidopropyl betaine. The reminder is a mixture of other fatty acid amidopropyl betaines.

EXAMPLES

% means % by weight unless defined differently.

The following compositions were prepared and evaluated. The compositions were prepared by mixing (if present in the composition): $C_{12-16}$ alkyl glucoside and/or cocoamidopropyl betaine, $C_{8-10}$ alkyl glucoside, an organic acid and isosorbide monooleate at ambient temperature (20° C.). The pH was adjusted to 3-4.5 with the organic acid.

| Tested combinations with different surfactants | Concentration/% | | | | | |
|---|---|---|---|---|---|---|
| | Example 1 | Example 2 | Example 3 | Example 4 | Example 5 | Example 6 |
| isosorbide monooleate | 25.2 | 25.2 | 25.2 | 25.2 | 25.2 | 25.2 |
| C12-16 APG | | | | | | 36 |
| C8/10 APG | | | | 36 | 29 | |
| C8-18 Cocoamidopropyl betaine | | | 29.2 | | | |
| Sodium Laureth Sulfate | 36 | 29 | | | | |
| Water | | | | up to 100 | | |
| Evaluation result | gel-like | gel-like | phase separation | phase separation | phase separation | gel-like |

| Tested combinations with different surfactants | Concentration/% | | | | | |
|---|---|---|---|---|---|---|
| | Example 7 | Example 8 | Example 9 | Example 10 | Example 11 | Example 12 |
| isosorbide monooleate | 25.2 | 25.2 | 25.2 | 25.2 | 25.2 | 25.2 |
| C12-16 APG | 29 | 17 | 12.5 | | 19 | 5.2 |
| C8/10 APG | | 20.8 | 16.5 | 18.9 | | 15.7 |
| C8-18 Cocoamidopropyl betaine | | | | 17.6 | 14.8 | 15.6 |
| Sodium Laureth Sulfate | | | | | | |
| Water | | | | up to 100 | | |
| Evaluation result | gel-like | ok | ok | ok | gel-like | ok | ok means that the viscosity was within a range that allowed easy processing and that no phase separation occurred during the experiment and during storage.

The isosorbide monooleate had a content of about 77% by weight monoester in which the acid moiety had a content of more than 75% by weight oleic acid moieties.

Conclusions:

| Combinations Tested | Result | Example referred to |
|---|---|---|
| ether sulfate | not suitable: gel-like | 1 and 2 |
| cocoamidopropyl betaine | not suitable: turbid, phase separation | 3 |
| C8/10 APG | not suitable: turbid, phase separation | 4 and 5 |
| C12-16 APG | not suitable: gel-like | 6 and 7 |
| C8/10 APG + C12-16 APG | suitable | 8 and 9 |
| C8/10 APG + cocoamidopropyl betaine | suitable | 10 |
| C12-16 APG + cocoamidopropyl betaine | not suitable: gel-like | 11 |
| C8/10 APG + C12-16 APG + cocoamidopropyl betaine | suitable | 12 |

A composition consisting of isosorbide monooleate (monoester content higher than 65%), a short chain APG (C8/10) and a long chain APG (C12-16) and/or cocoamidopropyl betaine resulted in a stable and easy to handle liquid.

The monoester content of isosorbide monooleate should be higher than 65% by weight (GC) due to stability and handling reasons of the composition obtained.

Examples Relating to Monooleate Content

The following compositions with different content of isosorbide monooleate ("pure isosorbide monooleate" as defined in the description) in the isosorbide monooleate used (mixture comprising pure isosorbide monooleate, dioleate, oleic acid and issorbide) were compared.

| monoester content of isosorbide monooleate | stability of composition (according to example 8) |
|---|---|
| 60% | instable: phase separation |
| 77% | stable and easy to handle |
| >95% | not easy to handle, gel-like behavior |

Formulation Examples

The following cosmetic formulations containing a composition according to the present invention have been made.

Formulation Example 1 (A Body Wash Formulation)

| Phase | Ingredients | INCI | % by weight |
|---|---|---|---|
| A | Water, demin. | Aqua | 73.55 |
| | Sodium Benzoate | Sodium Benzoate | 0.50 |
| B | Texapon ® N 70 | Sodium Laureth Sulfate | 14.50 |
| | Dehyton ® PK 45 | Cocamidopropyl Betaine | 5.50 |
| | Isosorbide Monoleate-APG-Compound (according to example 8) | | 4.00 |
| | Perfume | Parfum | q.s. |
| C | Citric Acid (50% solution) | Citric Acid | 0.55 |
| | Sodium Chloride | Sodium Chloride | q.s. | pH value (23° C.): 4.8

Viscosity (Brookfield; RVF; spindle 4; 20 rpm; 23° C.): 5000-7000 mPas

Mix the components of phase A. Add the components of phase B in the described order while stirring until the mixture is homogenous.

Adjust the pH with citric acid to pH 4.8-5.0. Adjust the viscosity with Sodium Chloride.

Formulation Example 2 (A Body Wash Formulation)

| Phase | Ingredients | INCI | % by weight |
|---|---|---|---|
| A | Dehyquart ® CC7 BZ | Polyquaternium-7 | 2.20 |
|   | Water, demin. | Aqua | 72.85 |
|   | Sodium Benzoate | Sodium Benzoate | 0.50 |
| B | Texapon ® N 70 | Sodium Laureth Sulfate | 13.00 |
|   | Dehyton ® PK 45 | Cocamidopropyl Betaine | 4.50 |
|   | Isosorbide Monoleate-APG-Compound (according to example 8) |  | 4.00 |
|   | Perfume | Parfum | q.s. |
| C | Citric Acid (50% solution) | Citric Acid | 0.55 |
|   | Sodium Chloride | Sodium Chloride | q.s. | pH value (23° C.): 4.8
Viscosity (Brookfield; RVF; spindle 4; 20 rpm; 23° C.): 6000-7000 mPas Mix the components of phase A. Add the components of phase B in the described order while stirring until the mixture is homogenous.

Adjust the pH with citric acid to pH 4.8-5.0. Adjust the viscosity with Sodium Chloride.

Formulation Example 3 (A Body Wash Formulation)

| Phase | Ingredients | INCI | % by weight |
|---|---|---|---|
| A | Texapon ® MC 120 | Sodium Laureth Sulfate, Cocamide MEA | 15.00 |
|   | Dehyton ® PK 45 | Cocamidopropyl Betaine | 3.00 |
|   | Plantacare ® 818 UP | Coco-Glucoside | 2.00 |
|   | Isosorbide Monoleate-APG-Compound (according to example 8) |  | 3.00 |
|   | Water, demin. | Aqua | 73.40 |
|   | Dehyquart ® CC7 BZ | Polyquaternium-7 | 2.20 |
| B | Sodium Benzoate | Sodium Benzoate | 0.50 |
|   | Perfume | Parfum | q.s. |
|   | Citric Acid (50% solution) | Citric Acid | 0.60 |
|   | Sodium Chloride | Sodium Chloride | q.s. | pH value (23° C.): 4.8-5
Viscosity (Brookfield; RVF; spindle 4; 20 rpm; 23° C.): 7000-10000 mPas Mix phase A at room temperature until homogeneous. Add components of phase B. Check pH and viscosity and adjust accordingly.

Formulation Example 4 (A Shower Bath)

| Phase | Ingredients | INCI | % by weight |
|---|---|---|---|
| A | Water, demin. | Aqua | 65.40 |
|   | Sulfopon ® 1216 G | Sodium Coco-Sulfate | 10.80 |
| B | Plantacare ® 818 UP | Coco-Glucoside | 19.30 |
|   | Isosorbide Monoleate-APG-Compound (according to example 8) |  | 4.00 |
|   | Sodium Benzoate | Sodium Benzoate | 0.50 |
|   | Perfume | Parfum | qs |
| C | Citric Acid (50% solution) | Citric Acid | qs |
|   | Sodium Chloride | Sodium Chloride | qs | pH value (23° C.): 5
Viscosity (Brookfield; RVF; spindle 4; 20 rpm; 23° C.): 6000-8000 mPas Heat phase A to 40° C. and mix until it has solved completely. Add phase B in the order as shown and mix until homogeneous. Adjust pH by adding citric acid (50%). Adjust the viscosity if necessary by adding Sodium Chloride.

The invention claimed is:

1. A composition comprising
   15-35% by weight isosorbide monooleate,
   10-30% by weight of a first surfactant selected from the group consisting of an alkyl glycoside having a weight average of the number of C-atoms in the alkyl chain of more than 11, cocoamidopropyl betaine, and mixtures thereof,
   10-30% by weight of a second surfactant which is an alkyl glycoside having a weight average of the number of C-atoms in the alkyl chain of less than 11,
   optionally an acid in an amount such that a pH value of the composition is 3 to 7,
   0-5% by weight further cosmetically acceptable ingredients, and
   balance water to 100% by weight.

2. The composition according to claim 1 comprising 20-30% by weight, isosorbide monooleate.

3. The composition according to claim 1 comprising 15-25% by weight of a first surfactant selected from the group consisting of an alkyl glycoside having a weight average of the number of C-atoms in the alkyl chain of more than 11, cocoamidopropyl betaine, and mixtures thereof.

4. The composition according to claim 1 comprising 15-25% by weight of the second surfactant.

5. The composition according to claim 1, wherein the first surfactant is an alkyl glycoside having a weight average of the number of C-atoms of more than 11.

6. The composition according to claim 1, wherein the first surfactant is cocoamidopropyl betaine.

7. The composition according to claim 1 comprising an organic acid in an amount such that the pH value of the composition is 3 to 7.

8. The composition according to claim 1 comprising
   23-28% by weight, isosorbide monooleate,
   17-22% by weight of an alkyl glycoside having a weight average of the number of C-atoms in the alkyl chain of more than 11,
   17-22% by weight, of an alkyl glycoside having a weight average of the number of C-atoms in the alkyl chain of less than 11,
   an organic acid in an amount such that the pH value of the composition is 3 to 7,
   balance water to 100% by weight.

9. The composition according to claim 1, wherein the composition is not a microemulsion.

10. The composition according to claim 1, wherein the composition comprises less than 5% by weight of an oil.

11. The composition according to claim 1, wherein the isosorbide monooleate is a mixture comprising pure isosorbide monooleate in an amount of 65-95% by weight.

12. The composition according to claim 1, wherein the alkyl glycosides present are alkyl glucosides, wherein the degree of oligomerization (number average) of the glucose moiety is between 1 and 2.

13. The composition according to claim 1, wherein the composition has a viscosity of between 1000 and 10000 mPas (determined with a Brookfield RVT viscometer, spindle 5, 20 rpm, at 20° C.).

14. A process for making the composition according to claim 1, wherein this process comprises
mixing the isosorbide monooleate, the first surfactant, the second surfactant, optionally the acid, optionally the further cosmetically acceptable ingredients and water, at a temperature of more than 20° C.

15. A cosmetic formulation, comprising
the composition according to claim 1, in an amount of 0.5 to 10% by weight,
and further cosmetically acceptable ingredients.

16. The composition according to claim 1, wherein the first surfactant is an alkyl glycoside having a weight average of the number of C-atom of more than 12.

17. The composition according to claim 1, wherein the second surfactant is an alkyl glycoside having a weight average of the number of C-atom of less than 10.

18. The composition according to claim 7 wherein the organic acid is selected from the group consisting of citric acid, lactic acid, and a mixture thereof.

19. The composition according to claim 11, wherein the isosorbide monooleate is a mixture comprising pure isosorbide monooleate in an amount of 65-85% by weight.

20. The cosmetic formulation of claim 15 wherein the formulation is a shampoo or a bodywash formulation.

* * * * *